United States Patent [19]

Schulte-Elte et al.

[11] 4,341,897
[45] Jul. 27, 1982

[54] PYRANIC DERIVATIVES FOR USE IN THE PREPARATION OF MUSCONE

[75] Inventors: Karl-Heinrich Schulte-Elte, Onex; Arnold Hauser, Petit-Lancy; Günther Ohloff, Bernex, all of Switzerland

[73] Assignee: Firmenich SA, Geneva, Switzerland

[21] Appl. No.: 249,117

[22] Filed: Mar. 30, 1981

Related U.S. Application Data

[62] Division of Ser. No. 96,054, Nov. 20, 1979, Pat. No. 4,277,625.

[30] Foreign Application Priority Data

Dec. 7, 1978 [CH] Switzerland ..................... 12510/78

[51] Int. Cl.$^3$ .......................................... C07D 311/00

[52] U.S. Cl. .................................................... 549/355
[58] Field of Search ..................................... 260/345.1

[56] References Cited

PUBLICATIONS

Schulte–Elte et al., Chem. Abstract, 92, 128,459y (1980) (Abstract of Helv. Chim. Acta, 1979, 62(8), pp. 2673–2680).

*Primary Examiner*—Nicky Chan
*Attorney, Agent, or Firm*—Pennie & Edmonds

[57] ABSTRACT

New process for the preparation of muscone, a valuable macrocyclic musky perfume ingredient. The process makes use of an $\alpha,\omega$-dialdehyde as starting material.

1 Claim, No Drawings

PYRANIC DERIVATIVES FOR USE IN THE PREPARATION OF MUSCONE

This is a division of application Ser. No. 096,054 filed Nov. 20, 1979 which issued on July 7, 1981 as U.S. Pat. No. 4,277,625.

BRIEF SUMMARY OF THE INVENTION

The invention relates to the field of perfumery, in particular it provides a process for the preparation of muscone (3-methyl-cyclopentadecanone). The new process of the invention makes use of dodeca-4,8-dien-1,12-dial or of dodecan-1,12-dial as starting materials and consists in the following subsequent steps:

a. subjecting to acetalyzation a dialdehyde of formula

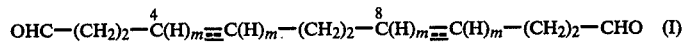

containing two single or two double bonds in positions 4 and 8 of the chain as indicated by the dotted lines and wherein index m stands for 1 or 2, to give a monoacetal of formula

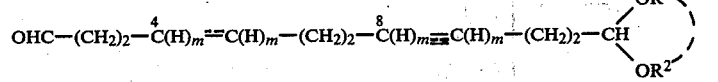

wherein each of symbols $R^1$ and $R^2$ represents, when taken separately, a lower alkyl radical, or when taken together, a lower alkylene radical, b. adding a methallyl-magnesium halide on the obtained mono-acetal to give a hydroxy derivative of formula

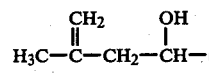

wherein symbols $R^1$ and $R^2$, index m and the dotted lines have the above given meaning, c. cyclizing by means of an acidic cyclization agent compound of formula (III) to yield a bicyclic oxygenated compound of formula

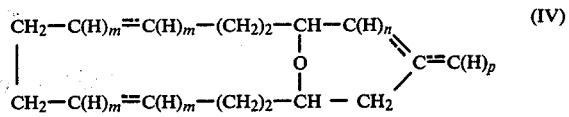

wherein index m and the dotted lines have the above indicated meaning and
 (a) n=1 and p=3 or
 (b) n=2 and p=2,
and d. subjecting said compound (IV) to an isomerization and a catalytic hydrogenation in an inert organic solvent to yield the desired muscone.

This invention provides also pyranic derivatives of formula

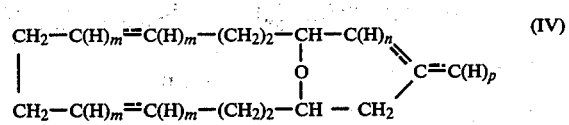

wherein indexes m, n and p and the dotted lines have the meaning given above.

BACKGROUND OF THE INVENTION

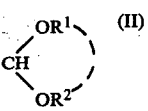

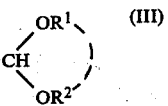

Among the most appreciated musky ingredients known in the art of perfumery, muscone, or 3-methyl-cyclopentadecanone, has acquired a special renown. Despite this fact, muscone has not found a widespread utilization in the art due to economical synthetic processes for its preparation.

Among the variety of known processes, one may cite the following:

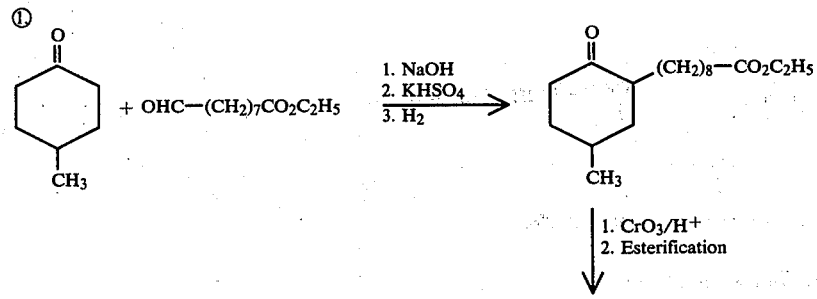

-continued
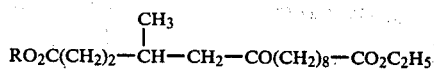
1. Acetal
2. Acyloin
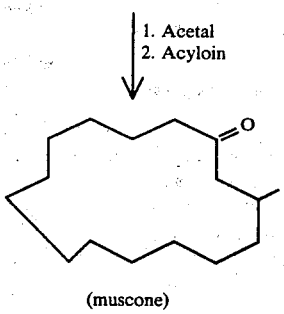
(muscone)
reference: J. Chem. Soc. 4154–7 (1964)
②
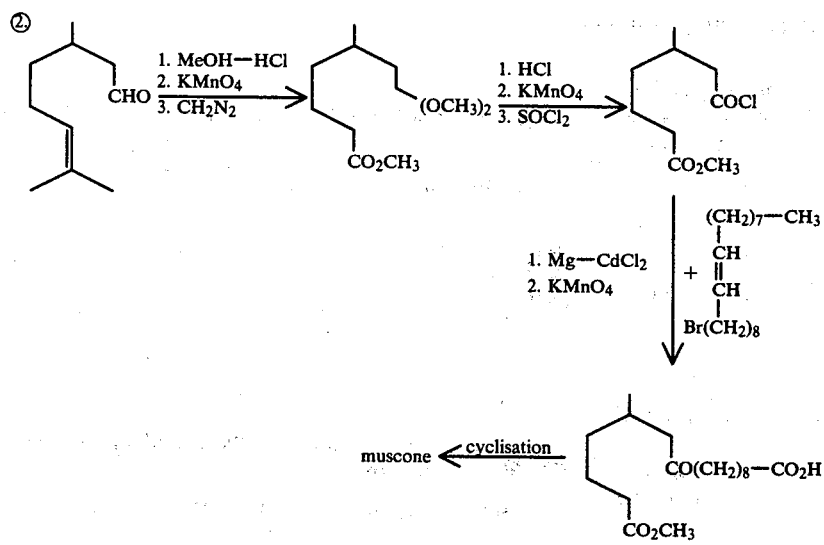
reference: Tetrahedron 20, 11, 2601 (1964)
③
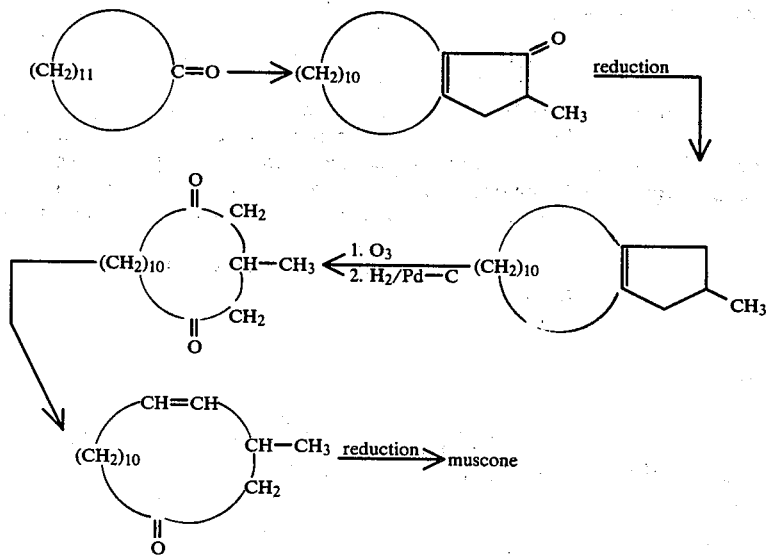
reference: Helv. Chim. Acta, 50, 705 (1967)
or the following variant:

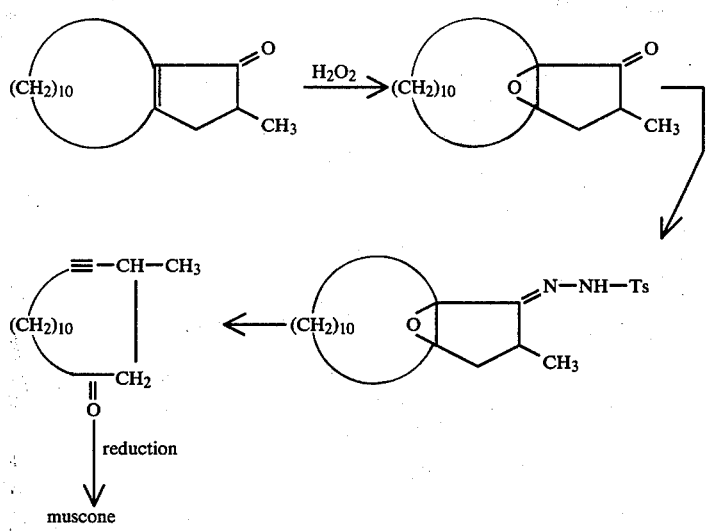

reference: Helv. Chim. Acta, 50, 708 (1967)

By making use of easily available starting materials, the process of the instant invention, which is characterized by a limited number of reaction steps, represents a new and original solution to the industrial preparation of muscone.

THE INVENTION

The process of the present invention can be illustrated by the following reaction scheme:

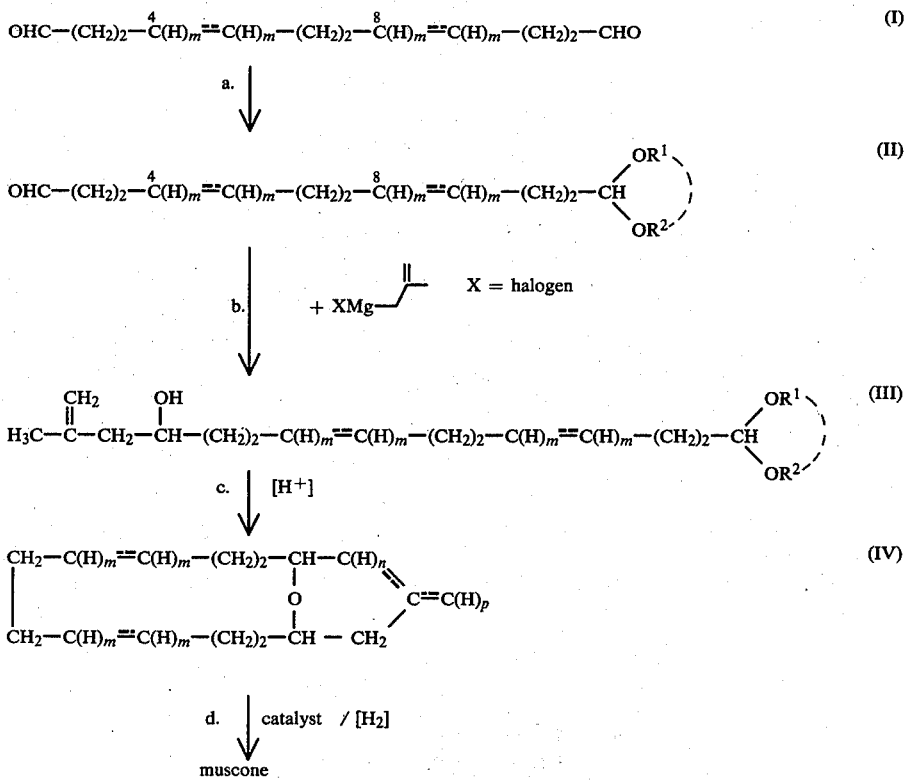

As indicated above, each of symbols $R^1$ and $R^2$ designates either a lower alkyl or alkylene radical. Thus they can represent a methyl, an ethyl or a propyl group, or an ethylene, a propylene or a tetramethylene radical.

Dodeca-4,8-diene-1,12-dial (see formula (I) wherein $m=1$), used as starting material in the process of the invention, is a readily available starting material which can be obtained from cyclododecatriene by means of a selective ozonization of one of the existing double bonds [see e.g. Swiss Pat. No. 577,445].

Dodecandial, [see formula (I) wherein $m=27$, also used as starting material in the process of the invention, can be synthesized according to the method described in Compt. Rend. 204, 1948 (1937).

Due to the presence of olefinic double bonds in their molecule, compounds (I) to (IV) can occur under the form of stereoisomers of different configuration, the process of the instant invention can be applied equally as well to either the pure isomers or any mixture thereof.

PREFERRED EMBODIMENTS OF THE INVENTION

The first step of the process of the invention, namely the mono-acetalyzation of dial (I) can be effected in accordance with known techniques, viz, in the presence of an acid catalyst, for example in the presence of acidic diatomaceous earth. Preferred reactants include ethylene glycol, which enables the preparation of ethylene acetal (II), wherein $R^1$ and $R^2$ taken together represent a divalent dimethylenic radical. After separation from the reaction mixture by means of fractional distillation, mono-acetal (II) is treated with a methallyl-magnesium halide and the resulting adduct is hydrolyzed under the conditions of a Grignard reaction. The thus obtained hydroxy derivative is cyclized by means of an acidic cyclization agent. Suitable acidic agents include protic mineral or organic acids and acidic diatomaceous earth. Such a cyclization is preferably carried out in an inert organic solvent, for instance an aliphatic, cycloaliphatic or aromatic hydrocarbon or an ether. We have observed that good yields of the end product could be obtained by carrying out the cyclization in the presence of p-toluenesulphonic acid in an aromatic hydrocarbon, such as toluene, at a temperature close to the boiling temperature of the chosen solvent, e.g. at about 100°–120° C. In order to avoid the formation of by-products, specially originating from condensation reactions, the cyclization is preferably effected by dissolving, at a high level of dilution, the starting hydroxy-acetal in the chosen solvent. To this end, concentrations of about 1 or 2% by weight are utilized.

The last step of the process, which consists in the isomerization and catalytic hydrogenation of the pyranic compound of formula (IV), can be carried out in the presence of the usual hydrogenation catalysts, e.g. Raney-nickel or palladium on charcoal.

According to a preferred embodiment, the step of isomerization and hydrogenation is effected in an inert organic solvent, for instance in an aromatic hydrocarbon such as xylene and at a temperature close to the boiling point thereof.

The invention is better illustrated by the following examples, wherein the temperatures are indicated in degrees centigrade.

EXAMPLE 1

Preparation of muscone a. Dodeca-4,8-dien-1,12-dial ethylene-mono-acetal

To a mixture, kept at reflux, of 970 g (5 M) of dodeca-4,8-dien-1,12-dial and 5 g of acidic diatomaceous earth in 5 lt of isopropyl ether in a vessel equipped with a water separator, there were added dropwise, within a period of 10–15 hours, and under vigorous stirring, 341 g (5.5 M) of ethylene-glycol. Once the addition was over, the reaction mixture was kept refluxing for 3–4 hours and 99 ml of water were isolated. After filtration and evaporation of the volatile fraction, there was obtained a residue (1200 g) which was then fractionally distilled to yield 488 g of the desired mono-acetal (purity of about 95%).

IR (film): 2700, 1720 cm$^{-1}$;

NMR (CDCl$_3$, 60 MHz): 1.5–2.6 (12H, m); 3.88 (4H, d, J=2.4); 4.84 (1H, t, J=4); 5.2–5.6 (4H, m); 9.77 (1H, s) δppm;

MS: M$^+$=238; m/e=220 (2), 195 (15), 175 (8), 163 (2), 141 (13), 119 (14), 99 (30), 73 (100), 55 (16), 41 (42), 29 (13).

b. 2-Methyl-4-hydroxy-pentadeca-1,7,11-trien-15-al ethylene acetal 2 ml of methallyl chloride were added dropwise, under vigorous stirring, to a suspension of 21.4 g (0.9 M) of magnesium turnings in 50 ml of anhydrous diethyl ether and 0.5 ml of ethyl bromide. To this suspension was then added within about 3 hours a solution of 119 g (0.5 M) of the mono-acetal obtained in sub letter (a) above and 90 g (1.0 M) of freshly distilled methallyl chloride in 1 lt of anhydrous ether and 250 ml of tetrahydrofuran. The addition was set at a rate such that the temperature of the reaction mixture was kept below 10°–15°; as a result which necessitated external cooling. The mixture was then kept under stirring at about 15°–20° for 3 hours, whereupon the clear solution obtained upon decanting the excess magnesium was hydrolyzed by means of a saturated aqueous solution of NH$_4$Cl and ice. The aqueous phase was extracted twice with ether and the combined organic extracts were washed with water and an aqueous solution of NaCl until neutralized.

After the usual treatments of drying and evaporation a raw material was obtained (142 g; yield 96%) which upon bulb distillation (160°–170°/0.1 Torr) gave 125 g of the desired hydroxy-acetal.

IR (film): 3345, 3080, 1642, 890 cm$^{-1}$;

NMR (CDCl$_3$, 60 MHz): 1.74 (3H, s); 3.5–4.1 (5H, m); 4.7–5.0 (3H, m); 5.2–5.6 (4H, m) δppm;

MS: (M$^+$−57)=237; m/e: 222 (1), 208, 195 (9), 177 (3), 159 (4), 147 (7), 141 (13), 129 (12), 119 (13), 109 (18), 99 (40), 93 (39), 79 (49), 73 (100), 67 (36), 55 (39), 43 (96), 31 (83).

c. Bicyclic ether of formula (IV), m=1; n=1; p=3 or n=2; p=2

To a refluxing solution of 500 mg of p-toluene-sulphonic acid in 500 ml of toluene was added a solution of 14.7 g (0.05 M) of the hydroxy-acetal obtained in sub letter (b) above. The reaction was effected in a vessel equipped with a water separator. Once the addition was over, an additional quantity of 200 mg of p-toluene sulphonic acid was added to the mixture and this was concentrated to roughly one half of its volume by evaporating a part of the toluene present. The concentrated mixture was washed twice with an aqueous solution of NaOH, dried over Na$_2$SO$_4$ and evaporated under reduced pressure.

There were thus obtained 13.3 g of a residue which upon distillation in a bulb apparatus gave at 110°–120°/0.1 Torr 8 g (yield 69%) of bicyclic ether (IV) having a purity of about 95%.

NMR (CDCl$_3$, 90 MHz): 1.66 (3H, d, J=2); 3.2–3.6 (1H, m); 3.7–4.1 (1H, m); 4.15–6.9 (5H, m) δppm;

MS: M+=232 (48); m/e: 217 (6), 203 (11), 189 (19), 175 (7), 163 (24), 147 (36), 135 (38), 121 (86), 109 (75), 95 (100), 79 (83), 67 (73), 55 (57), 41 (99).

d. Muscone 2800 mg of palladium on charcoal at 10% in suspension in 50 ml of refluxing xylene were activated during 2 hours by exposing the suspension to a continue flow of hydrogen (flow rate: 40 ml/min.). To this mixture were then added 6960 mg (0.03 M) of the bicyclic ether obtained according to letter c. above and the whole was kept under reflux during 7-8 hours while keeping the flow of hydrogen. The course of the reaction was followed by means of a chromatographic analysis. The excess of hydrogen was eliminated by bubbling through the mixture a flow of nitrogen and the catalyst was recovered by filtration. After concentration of the reaction mixture followed by a fractional distillation with a micro Fisher type apparatus there were obtained 5.0 g (yield 70%) of muscone: B.p. 25°–65°/0.1 Torr.

EXAMPLE 2

By operating in an manner identical to that described above, and using as starting material the ethylene monoacetal of dodecandial instead of the ethylene monoacetal of dodeca-4,8-dien-1,12-dial, muscone was obtained in a lower yield.

a. Dodecan-1,12-dial ethylene mono-acetal yield: 10–20%;
IR: 2710, 1725 cm$^{-1}$;
NMR (CDCl$_3$, 60 MHz): 2.1–2.6 (2H, m); 3.6–4.1 (4H, m); 4.83 (1H, t, J=4); 9.75 (1H, t, J=2) δppm; MS: M$^+$=242 (<1); m/e: 113 (<1), 95 (<1), 73 (32), 62 (4), 43 (13), 31 (100).

b. 2-Methyl-4-hydroxy-pentadecan-15-al ethylene monoacetal yield: 95%;
IR: 3500, 3130, 1655, 890 cm$^{-1}$;
NMR (CDCl$_3$, 60 MHz): 1.75–2.3 (6H, m); 2.1 (1H, m); 3.5–4.1 (5H, m); 4.7–5.0 (3H, m) δppm;

MS: (M$^+$−85)=213 (<1); 200 (<1), 180 (<1), 163 (1), 144 (2), 124 (10), 109 (7), 89 (28), 81 (6), 73 (22), 63 (13), 56 (100), 43 (70), 31 (56).

c. Bicyclic ether of formula (IV), (m=2; n=1; p=3 or n=1; p=2)

yield 15–20%;
NMR (CDCl$_3$, 60 MHz): 1.1–2.2 (25H, m); 3.2–3.65 (1H, m); 3.8–4.2 (1H, m); 5.24 (1H, m) δppm;
MS: M$^+$=236 (17); m/e: 221 (11), 207 (1), 194 (4), 178 (5), 163 (2), 149 (4), 135 (8), 121 (22), 109 (34), 95 (100), 81 (43), 67 (39), 55 (54), 41 (59), 29 (20).

This ether could also be obtained, in a 95% yield, from the unsaturated bicyclic ether obtained according to Example 1—see paragraph (c), by hydrogenating it in the presence of a Lindlar type catalyst.

d. Muscone, prepared by treating the obtained bicyclic ether with hydrogen in the presence of palladium on charcoal, showed analytical characters identical in all respects with those of a pure sample.

What we claim is:
1. A pyranic compound having the formula:

$$\begin{array}{c} CH_2-C(H)_m=C(H)_m-(CH_2)_2-CH-C(H)_n \\ | \qquad\qquad\qquad\qquad\qquad | \qquad\quad \diagdown \\ | \qquad\qquad\qquad\qquad\qquad O \qquad\quad C=C(H)_p \\ | \qquad\qquad\qquad\qquad\qquad | \qquad\quad \diagup \\ CH_2-C(H)_m=C(H)_m-(CH_2)_2-CH-CH_2 \end{array} \qquad (IV)$$

wherein m represents 1 or 2, as a result which necessitated external cooling and n represents 1 and p represents 3 and the bond between C and C(H)$_p$ is a single bond and the bond between C(H)$_n$ and C is a double bond or n represents 2 and p represents 2 and the bond between C and C(H)$_p$ is a double bond and the bond between C(H)$_n$ and C is a single bond.

* * * * *